United States Patent
Dunn et al.

(10) Patent No.: US 6,667,398 B2
(45) Date of Patent: Dec. 23, 2003

(54) PROCESS FOR THE PREPARATION OF PYRAZOLOPYRIMIDINONES

(75) Inventors: Peter James Dunn, County of Kent (GB); Catherine Dunne, County of Kent (GB)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/886,269

(22) Filed: Jun. 21, 2001

(65) Prior Publication Data

US 2002/0013464 A1 Jan. 31, 2002

Related U.S. Application Data

(60) Provisional application No. 60/217,769, filed on Jul. 12, 2000, and provisional application No. 60/291,100, filed on May 16, 2001.

(30) Foreign Application Priority Data

Jun. 22, 2000 (GB) ............................................. 0015472
Mar. 9, 2001 (GB) ............................................. 0105857

(51) Int. Cl.$^7$ ........................................... C07D 487/04
(52) U.S. Cl. ........................ 544/262; 544/238; 544/118
(58) Field of Search ................................ 544/262, 238, 544/118

(56) References Cited

FOREIGN PATENT DOCUMENTS

| EP | 0463756 | 1/1992 | ......... C07D/487/04 |
| EP | 0812845 | 12/1997 | ......... C07D/487/04 |
| EP | 0994115 | 4/2000 | |
| EP | 1002798 | 5/2000 | |
| WO | 94/28902 | 12/1994 | ......... A61K/31/505 |
| WO | 98/54333 | 12/1998 | ........... C12N/15/57 |

OTHER PUBLICATIONS

J. March, Advanced Organic Chemistry, 3rd Ed. Chpt 10, 371–374, John Wiley & Sons 1985.
Comprehensive Organic Functional Group Transformations, 1st Ed. vol. 5, Sections 5.17 (p. 653) and 5.19 (p. 741), Pergamon Press 1995.
XP–002177561 Rotella, et al., J. Med. Chem. 2000, 43, 1257–1263.
XP–002920282 Schneller, et al., J. Org. Chem. vol 51, No. 21, 1986.
XP–001007465 Parkin, et al., J. Heterocyclic Chem, 19, 33, 1982.
XP–002024136 Costanzo, et al., J. Med. Chem. 1996, 39, 3039–3043.

Primary Examiner—John M. Ford
(74) Attorney, Agent, or Firm—Peter C. Richardson; Gregg C. Benson; James T. Jones

(57) ABSTRACT

There is provided a process for the production a compound of general formula I:

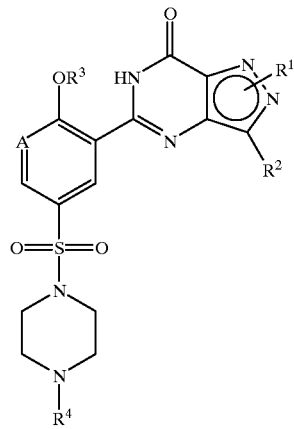

wherein A, $R^1$, $R^2$, $R^3$ and $R^4$ have meanings given in the description, which process comprises the reaction of a compound of formula II,

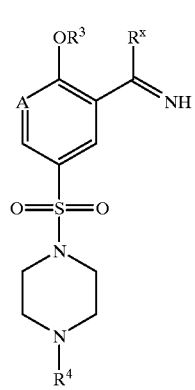

wherein $R^x$ is a group substitutable by an aminopyrazole, with a compound of general formula III

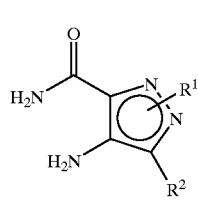

16 Claims, No Drawings

PROCESS FOR THE PREPARATION OF PYRAZOLOPYRIMIDINONES

This application is filed claiming priority from co-pending Provisional Application Nos. 60/217,769 filed Jul. 12, 2000 and 60/291,100 filed May 16, 2001.

This invention relates to a novel process for the production of 4-alkylpiperazinylsulfonylphenyl- and 4-alkylpiperazinylsulfonyl pyridinyl-dihydropyrazolo[4,3-d]pyrimidin-7-one derivatives, and, in particular, the anti-impotence drug, sildenafil and analogues thereof.

Sildenafil (5-[2-ethoxy-5-(4-methylpiperazin-1-ylsulfonyl)phenyl]-1-methyl-3-n-propyl-1,6-dihydro-7H-pyrazolo[4,3-d]pyrimidin-7-one),

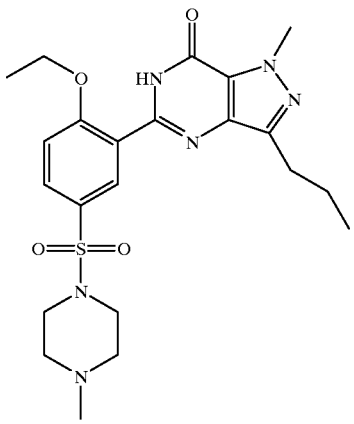

is the active ingredient in Viagra™. The compound, which was originally disclosed in European patent application EP 463 756, has been found to be particularly useful in the treatment of inter alia male erectile dysfunction (see international patent application WO 94/28902).

Multi-step syntheses for the preparation of sildenafil are described in EP 463 756. An improved process for its production is described in a later application (European patent application EP 812 845), the final step of which involves an internal cyclisation under basic, neutral or acidic conditions.

We have now found that sildenafil and analogues thereof may be made via a novel process, as described hereinafter, which process has advantages over the processes described in the above-mentioned prior art documents.

According to a first aspect of the invention, there is provided a process for the production of compounds of general formula I:

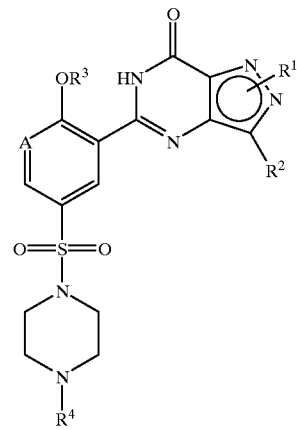

wherein
A represents CH or N;
$R^1$ represents H, lower alkyl (which alkyl group is optionally interrupted by O), Het, alkylHet, aryl or alkylaryl, which latter five groups are all optionally substituted (and/or, in the case of lower alkyl, optionally terminated) by one or more substituents selected from halo, cyano, nitro, lower alkyl, $OR^5$, $C(O)R^6$, $C(O)OR^7$, $C(O)NR^8R^9$, $NR^{10a}R^{10b}$ and $SO_2NR^{11a}R^{11b}$;
$R^2$ and $R^4$ independently represent lower alkyl;
$R^3$ represents lower alkyl, which alkyl group is optionally interrupted by oxygen;
Het represents an optionally substituted four- to twelve-membered heterocyclic group, which group contains one or more heteroatoms selected from nitrogen, oxygen and sulfur;
$R^5$, $R^6$, $R^7$, $R^8$, $R^9$, $R^{11a}$ and $R^{11b}$ independently represent H or lower alkyl; $R^{10a}$ and $R^{10b}$ either independently represent, H or lower alkyl or, together with the nitrogen atom to which they are attached, represent azetidinyl, pyrollidinyl or piperidinyl, which process comprises the reaction of a compound of formula II,

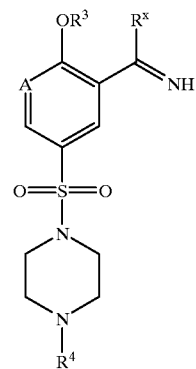

wherein $R^x$ is a group substitutable by an aminopyrazole and A, $R^3$ and $R^4$ are as defined above, with a compound of general formula III,

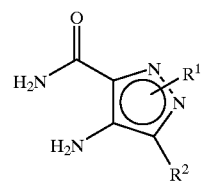

wherein R¹ and R² are as defined above, which process is referred to hereinafter as "the process of the invention".

The compounds of the general formulae I and III may be represented by either of the formulae I, IA and IB or IIIA or IIIB in the process according to the present invention.

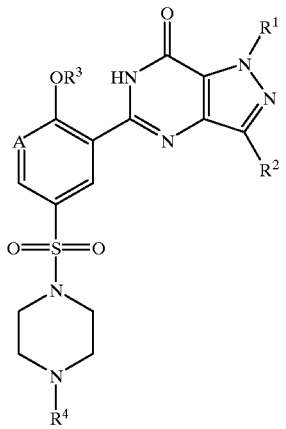

IA

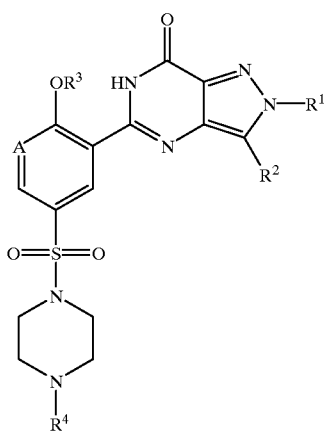

IB

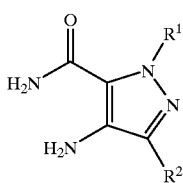

IIIA

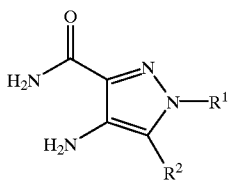

IIIB

The term "aryl", when used herein, includes six- to ten-membered carbocyclic aromatic groups, such as phenyl and naphthyl and the like.

Het groups may be fully saturated, partly unsaturated, wholly aromatic, partly aromatic and/or bicyclic in character. Het groups that may be mentioned include groups such as optionally substituted azetidinyl, pyrrolidinyl, imidazolyl, indolyl, oxadiazolyl, thiadiazolyl, triazolyl, tetrazolyl, oxatriazolyl, thiatriazolyl, pyridazinyl, morpholinyl, pyrimidinyl, pyrazinyl, pyridyl, quinolinyl, isoquinolinyl, piperidinyl, pyrazolyl, imidazopyridinyl, piperazinyl, thienyl and furanyl.

The point of attachment of any Het group may be via any atom in the ring system including (where appropriate) a heteroatom. Het groups may also be present in the N- or S-oxidised form.

The term "lower alkyl" (which includes the alkyl part of alkylHet and alkylaryl groups), when used herein, includes $C_{1-6}$ alkyl (e.g. $C_{1-4}$ alkyl). Unless otherwise specified, alkyl groups may, when there is a sufficient number of carbon atoms, be linear or branched, be saturated or unsaturated, be cyclic, acyclic or part cyclic/acyclic, and/or be substituted by one or more halo atoms.

As defined herein, the term "halo" includes fluoro, chloro, bromo and iodo.

Compounds of formulae I, IA and IB may contain one or more asymmetric carbon atoms and may therefore exhibit optical and/or diastereoisomerism. The process of the invention thus also relates to the formation of stereoisomers of compounds of formulae I, IA and IB and mixtures thereof. Stereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation, or by derivatisation, for example with a homochiral acid followed by separation of the diastereomeric esters by conventional means (e.g. HPLC, crystallisation, chromatography over silica or, for example, via classical resolution with a homochiral acid salt). The formation of all stereoisomers is included within the scope of the invention.

Compounds of formula II may exhibit tautomerism. The use of all tautomeric forms of the compounds of formula II is included within the scope of the invention.

Preferred compounds of formulae I, IA and IB include those in which:

$R^1$ represents $C_{1-4}$ alkyl, which alkyl group is optionally interrupted by an oxygen atom, and/or is optionally terminated by a Het group (such as a pyridinyl group);

$R^2$ represents $C_{1-4}$ alkyl;

$R^3$ represents $C_{1-5}$ alkyl, which alkyl group is optionally interrupted by an oxygen atom;

$R^4$ represents $C_{1-3}$ alkyl.

More preferred compounds of formulae I, IA and IB include those in which:

$R^1$ represents linear $C_{1-3}$ alkyl, which alkyl group is optionally interrupted by an oxygen atom, or is optionally terminated by a 2-pyridinyl group (e.g. to form a 2-pyridinylmethyl group);

$R^2$ represents linear $C_{2-3}$ alkyl;

$R^3$ represents linear or branched $C_{2-4}$ alkyl, which alkyl group is optionally interrupted by an oxygen atom;

$R^4$ represents $C_{1-2}$ alkyl.

Particularly preferred compounds that may be formed in the process of the invention include sildenafil, and the following four compounds:

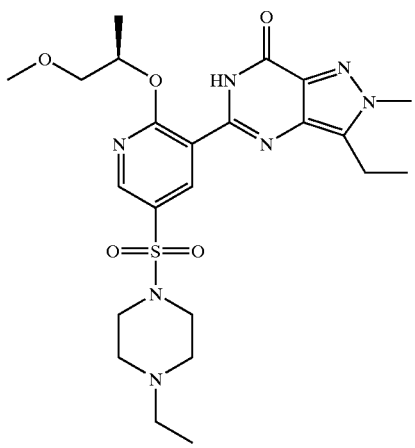

1B

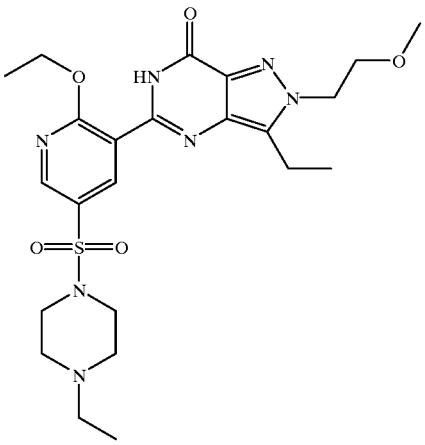

1E

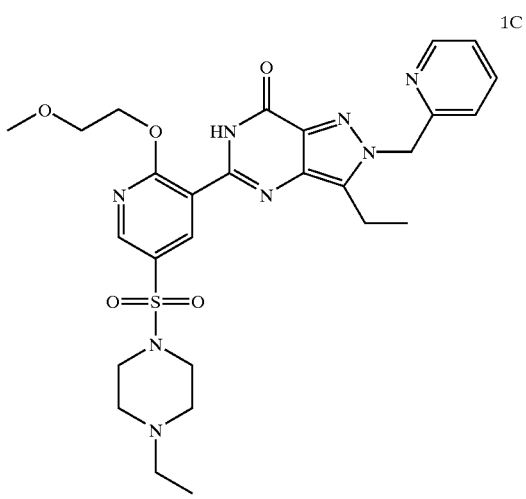

1C

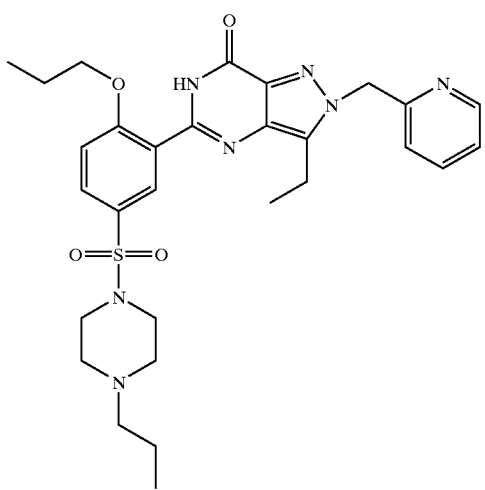

1D

Said compounds 1B, 1C, 1D and 1E are otherwise known as: 1B, (+)-3-ethyl-5-[5-(4-ethylpiperazin-1-ylsulphonyl)-2-(2-methoxy-1(R)-methylethoxy)pyridin-3-yl]-2-methyl-2,6-dihydro-7H-pyrazolo[4,3-d]pyrimidin-7-one also known as 3-Ethyl-5-{5-[4-ethylpiperazin-1-ylsulphonyl]-2-([(1R)-2-methoxy-1-methylethyl]oxy)pyridin-3-yl}-2-methyl-2,6-dihydro-7H-pyrazolo[4,3-d]pyrimidin-7-one, the compound of Example 118 of WO99/54333; 1C, 3-ethyl-5-[5-(4-ethylpiperazin-1-ylsulphonyl)-2-n-propoxyphenyl]-2-(pyridin-2-yl)methyl-2,6-dihydro-7H-pyrazolo[4,3-d]pyrimidin-7-one, the compound of Example 5 of WO98/49166; 1D, 3-ethyl-5-[5-(4-ethylpiperazin-1-ylsulphonyl)-2-(2-methoxyethoxy)pyridin-3-yl]-2-(pyridin-2-yl)methyl-2,6-dihydro-7H-pyrazolo[4,3-d]pyrimidin-7-one, the compound of Example 4 of WO99/54333; and 1E, 5-[2-Ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, also known as 1-{6-ethoxy-5-[3-ethyl-6,7-dihydro-2-(2-methoxyethyl)-7-oxo-2H-pyrazolo[4,3-d]pyrimidin-5-yl]-3-pyridyl sulphonyl}-4-ethylpiperazine, the compound of Example 8 of IB00/01457, exemplified hereinafter as Example 3.

By "group substitutable by an aminopyrazole having structure III" we include any group which, when present in the moiety —C($R^x$)=NH of a compound of formula II, may undergo displacement by the amino group of an aminopyrazole such that a —C(=NH)—NH— linkage is thereby formed. In accordance with the process of the invention, which the skilled person will appreciate involves a "one-pot" condensation/cyclisation reaction, the aminopyrazole that is reacted with the compound of formula II is a compound of formula III, IIIA or IIIB. Following the condensation reaction, the coupled intermediate undergoes cyclisation to form a compound of general formula I.

In this respect, preferred groups that $R^x$ may represent include —NH$_2$, —NHR$^a$, —N(R$^b$)R$^c$, —SR$^d$, —SH, —OR$^e$ wherein groups R$^b$ to R$^e$ each independently represent the same groups that R$^1$ as hereinbefore defined may represent (except that they do not represent H or alkoxy) as well as halo (e.g. chloro). Group R$^a$ represents —OR$^1$ or halo (e.g. chloro) wherein R$^1$ is as hereinbefore defined. More preferred values of R$^x$ include —NHR$^a$, —N(R$^b$)R$^c$, and preferably —SR$^d$, —SH and —OR$^e$. Particularly preferred values of R$^x$ are C$_{1-4}$ alkoxy (e.g. ethoxy).

According to a further aspect of the invention, there is provided a process for the production of a compound of formula I, IA or IB, as hereinbefore defined, which process comprises the reaction of a compound of formula III, IIIA or IIIB (as appropriate), as hereinbefore defined, with a compound of formula II, as hereinbefore defined, provided that R$^x$ does not represent —NH$_2$, or, preferably, R$^x$ does not represent —NH$_2$, —NHR$^a$ or —N(R$^b$)R$^c$.

The process of the invention may be carried out in the presence of a suitable organic solvent system, which solvent system should not significantly react chemically with, or significantly give rise to stereochemical changes in, the reactants or product once formed, or significantly give rise to other side reactions. Preferred solvent systems include aromatic hydrocarbons (e.g. toluene or xylene) or chlorobenzene. Preferred solvent systems also include solvents of formula $R^xH$, for example, solvents of formula $R^eOH$ (e.g. ethanol), wherein $R^x$ and $R^e$ are as hereinbefore defined.

In the process of the invention, it may be preferable to add compounds of formulae III, IIIA or IIIB to the reaction mixture (prior to carrying out the reaction) in a suitable polar organic solvent such as ethyl acetate. Such a polar solvent may then be removed before the reaction is initiated.

The process of the invention may be carried at elevated temperature (e.g. up to the reflux temperature of the relevant solvent system, or higher if a pressurised system is employed). Clearly, appropriate reaction times and reaction temperatures depend upon the solvent system that is employed, as well as the reactants that are used and the compound that is to be formed, but these may be determined routinely by the skilled person.

We have found that compounds of formula II may be prepared, advantageously, by way of reaction of a compound of formula IV,

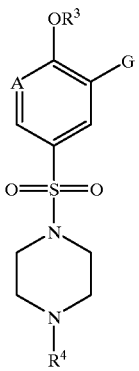

IV wherein G represents a carboxylic acid group (—C(O)OH) or a derivative thereof, and A, $R^3$ and $R^4$ are as hereinbefore defined, with an appropriate reagent for converting the group G to a —C($R^x$)=NH group, wherein $R^x$ is as hereinbefore defined.

The term "derivative of a carboxylic acid group" when used herein includes groups which are commonly derived from a carboxylic acid and/or groups that contain a central carbon atom (which carbon atom is attached to the phenyl or pyridyl ring in the compound of formula IV) that is at the same oxidation state as —C(O)OH. The term therefore includes groups such as —CN, —C($OR^e$)$_3$, —C(O)NH$_2$ or —C(=$NOR^f$)N($R^e$)$_2$, wherein $R^f$ represents H or lower alkyl and $R^e$ is as hereinbefore defined. G can also represent a 5- or 6-membered heterocyclic group containing at least two heteroatoms selected from O, S, N and mixtures thereof wherein said heterocyclic group is bonded by a carbon atom, a preferred heterocyclic group, as exemplified in preparation 4 herein, has the general formula —C(=$NOR^g$)N($R^e$) wherein the carbon is bonded to both N atoms and wherein $R^g$ is bonded to the N of the —$NR^e$ group and wherein $R^g$ is a —CH, or a —CH$_2$— group and wherein $R^e$ is as defined hereinbefore and is preferably H or lower alkyl or lower alkoxy.

Preferred compounds of formula IV include those in which, when A represents CH, then G does not represent —C(O)OH.

Procedures for the conversion of selected groups which G may represent to certain —C($R^x$)=NH groups are known to those skilled in the art, and are described inter alia in: J. March, Advanced Organic Chemistry, 3$^{rd}$ Edition, Chapter 10, 371–374, John Wiley & Sons (1985); and Comprehensive Organic Functional Group Transformations, edited by A. Katritzky, O. Meth-Cohn, and C. Rees, 1$^{st}$ Edition, Volume 5, Sections 5.17 (page 653) and 5.19 (page 741), Pergamon Press (1995), the disclosures of which documents are hereby incorporated by reference. For example, compounds of formula II may be prepared by way of the following procedures.

1) For compounds of formula II in which $R^x$ represents —$OR^e$ (wherein $R^e$ represents lower alkyl (optionally interrupted by O), alkylHet or alkylaryl, e.g. lower alkyl):

(a) a corresponding compound of formula IV in which G represents —CN may be reacted with an alcohol of formula VA, $$R_\alpha OH \qquad \text{VA}$$

wherein $R_\alpha$ represents lower alkyl (optionally interrupted by O), alkylHet or alkylaryl (e.g. lower alkyl), and Het is as hereinbefore defined, in the presence of a suitable protic acid (e.g. HCl gas) and optionally in the presence of an appropriate solvent (e.g. diethyl ether, dioxan, benzene or chloroform). The skilled person will appreciate that such a reaction may be performed at low temperature (e.g. below 5° C.);

(b) a corresponding compound of formula IV in which G represents —C(O)NH$_2$ may be reacted with an appropriate alkylating agent of formula VB, $$R_\alpha - Z^1 \qquad \text{VB}$$

wherein $Z^1$ represents a leaving group such as halo, —OS(O)$_2$$OR_\alpha$, —OS(O)$_2$CF$_3$ or $OR_{\alpha 2}$, and $R_\alpha$ is as hereinbefore defined, optionally in the presence of a suitable solvent (e.g. dichloromethane), followed by deprotonation of the resulting alkoxymethyleneiminium salt in the presence of a suitable base (e.g. NaOH or a tertiary amine such as triethylamine); or (c) a corresponding compound of formula IV in which G represents —C($OR_\alpha$)$_3$, wherein $R_\alpha$ is as hereinbefore defined, may be reacted with ammonia, or an N-protected derivative thereof, for example in the presence of a catalytic quantity of a suitable acid (e.g. a protic acid such as p-toluenesulfonic acid), and optionally in the presence of an appropriate solvent (e.g. dichloromethane).

2) For compounds of formula II in which $R^x$ represents —$OR^e$ (wherein $R^e$ represents Het or aryl, e.g. phenyl), a corresponding compound of formula IV in which G represents —CN may be reacted with a compound of formula VC, $$R_\beta OH \qquad \text{VC}$$

wherein $R_\beta$ represents Het or aryl (e.g. phenyl), and Het is as hereinbefore defined, for example in the presence of a suitable catalyst (e.g. a Lewis acid such as ZnCl$_2$ and/or a protic acid such as HCl) and optionally in the presence of an appropriate solvent (e.g. dichloromethane).

3) For compounds of formula II in which $R^x$ represents —NH$_2$:

(a) a corresponding compound of formula IV in which G represents —CN may be reacted with hydrazine, hydroxylamine or O-lower alkyl hydroxylamine, followed by reduction of the resultant intermediate under standard conditions (e.g. palladium-catalysed hydrogenation); or (b) a corresponding compound of formula IV in which G represents —C(=NOR$^f$)N(R$^e$)$_2$, wherein R$^f$ is as hereinbefore defined, may be reduced under standard conditions (e.g. palladium-catalysed hydrogenation).

4) For compounds of formula II in which R$^x$ represents —NH$_2$, —NHR$^a$ or —N(R$^b$)R$^c$, a corresponding compound of formula IV in which G represents —CN may be reacted with a compound of formula VD, $$HN(R_\chi)(R_\delta) \qquad \text{VD}$$

wherein R$_\chi$ and R$_\delta$ independently represent H or R$^a$, and R$^a$ is as hereinbefore defined, for example in the presence of a suitable catalyst (e.g. a copper(I) salt such as CuCl) and optionally in the presence of an appropriate solvent (e.g. dimethylsulfoxide or a lower alkyl alcohol such as methanol or ethanol).

5) For compounds of formula II in which R$^x$ represents —SH:

(a) a corresponding compound of formula IV in which G represents —CN may be reacted with hydrogen sulfide, for example in the presence of a suitable base (e.g. a tertiary amine such as triethylamine) and optionally in the presence of an appropriate solvent (e.g. a lower alkyl alcohol such as ethanol); or (b) a corresponding compound of formula IV in which G represents —C(O)NH$_2$ may be reacted with a reagent that effects oxygen-sulfur exchange (e.g. P$_4$S$_{10}$ or Lawesson's reagent), for example in the presence of an appropriate solvent (e.g. toluene).

6) For compounds of formula II in which R$^x$ represents —SR$^d$, a corresponding compound of formula IV in which G represents —CN may be reacted with a compound of formula VE, $$R^dSH \qquad \text{VE}$$

wherein R$^d$ is as hereinbefore defined, for example in the presence of a suitable base (e.g. a tertiary amine such as triethylamine) and optionally in the presence of an appropriate solvent (e.g. a lower alkyl alcohol such as ethanol).

7) For compounds of formula II in which R$^x$ represents halo (e.g. chloro), a corresponding compound of formula IV in which G represents —C(O)NH$_2$ may be reacted with a suitable halogenating agent (e.g. a chlorinating agent such as PCl$_5$ or S(O)Cl$_2$), optionally in the presence of an appropriate solvent (e.g. benzene, CCl$_4$, CHCl$_3$ or dichloromethane).

Compounds of formula II may similarly be prepared from other compounds of formula II by reaction with a reagent that will convert one R$^x$ group to another. In this respect, compounds of formula II may additionally be prepared by way of the following procedures.

I) For compounds of formula II in which R$^x$ represents OR$^e$ (wherein R$^e$ represents lower alkyl, alkylHet or alkylaryl, e.g. lower alkyl), a corresponding compound of formula II in which R$^x$ represents Cl may be reacted with a compound of formula VA, as hereinbefore defined, for example in the presence of an appropriate solvent (e.g. dichloromethane) and a suitable base (e.g. an alkali metal alkoxide such as sodium ethoxide, or a tertiary amine such as triethylamine).

II) For compounds of formula II in which R$^x$ represents —NH$_2$, —NHR$^a$ or —N(R$^b$)R$^c$, a corresponding compound of formula II in which R$^x$ represents Cl, —SH, —SR$^d$ or —OR$^e$, wherein R$^d$ and R$^e$ are as hereinbefore defined, may be reacted with an appropriate compound of formula VD, as hereinbefore defined, or an acid (e.g. hydrogen chloride or CH$_3$C(O)OH) addition salt thereof, for example optionally in the presence of an appropriate solvent (e.g. dichloromethane, ethanol, diethyl ether, dioxan, benzene or chloroform) and/or a suitable reaction promoter (for example: for reaction of compounds of formula II in which R$^x$ represents —SH, a mercury(II) salt to act as a sulfide scavenger; and for reaction of compounds of formula II in which R$^x$ represents —SR$^d$, a pH buffer (e.g. sodium acetate/acetic acid)).

III) For compounds of formula II in which R$^x$ represents —SR$^d$, a corresponding compound of formula II in which R$^x$ represents —SH may be reacted with a compound of formula VF, $$R^d—Z^2 \qquad \text{VF}$$

wherein Z$^2$ represents a leaving group such as halo (e.g. iodo), alkanesulfonate, perfluoroalkanesulfonate (e.g. trifluoromethane-sulfonate) or arenesulfonate (e.g. p-toluenesulfonate), and R$^d$ is as hereinbefore defined, optionally in the presence of an appropriate solvent (e.g. dichloromethane or acetone) and/or a suitable base (e.g. a tertiary amine such as triethylamine).

Compounds of formula IV may be prepared via a variety of techniques. For example:

(a) Compounds of formula IV may be prepared by reaction of a compound of formula VI,

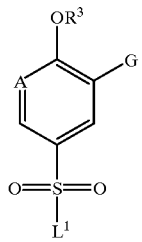

VI wherein L$^1$ is a leaving group (e.g. halo) and A, G and R$^3$ are as hereinbefore defined, with a compound of formula VII,

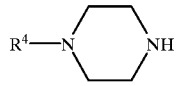

VII wherein R$^4$ is as hereinbefore defined. This reaction may be performed at, for example, low temperatures (e.g. between −10° C. and room temperature), in the presence of an appropriate solvent (e.g. a C$_{1-3}$ alcohol, ethyl acetate, dichloromethane, toluene or heptane), at least one equivalent of the compound of formula VII and, optionally, another suitable base (such as a base that does not react with or, if it does react, a base that further activates the sulfonyl chloride (for example: a tertiary amine such as triethylamine, N-ethyldiisopropylamine, 1,5-diazabicyclo[4.3.0]non-5-ene or 1,8-diazabicyclo[5.4.0]undec-7-ene; or a metal hydride, oxide, carbonate or bicarbonate)).

Compounds of formula VI are available using known techniques. For example, compounds of formula VI may be prepared from a corresponding compound of formula VIII,

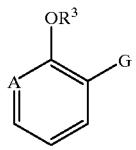

wherein A, G and $R^3$ are as hereinbefore defined, for example using conventional methods for the introduction of a —$SO_2L^1$ group into an aromatic or heteroaromatic ring system, such as reaction of a compound of formula VIII, optionally in the presence of an appropriate solvent (e.g. dichloromethane), with a compound of formula $L^1SO_3H$ and (optionally) a compound of formula $SO(L^1)_2$. When $L^1$ is chloro, reaction may take place at between 0° C. and room temperature in the presence of an excess of chlorosulfonic acid (optionally in conjunction with an excess of thionyl chloride), and optionally in an appropriate organic solvent (e.g. dichloromethane).

(b) Compounds of formula IV in which G represents —CN or —C(O)NH$_2$ may be prepared by reaction of a compound of formula IX,

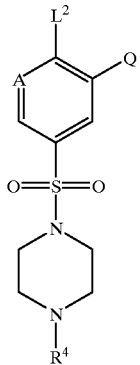

wherein Q represents —CN or —C(O)NH$_2$, $L^2$ represents a suitable leaving group and A and $R^4$ are as hereinbefore defined, for example by reaction with a compound that will provide the group $R^3O$ (e.g. an alkoxide base). This route is preferred for the preparation of compounds of formula IV in which A represents N.

Suitable leaving groups $L^2$ include standard groups known to those skilled in the art, such as optionally substituted arylsulfonyloxy groups (e.g. p-toluenesulfonyloxy), optionally substituted $C_{1-4}$ alkanesulfonyloxy groups (e.g. methanesulfonyloxy, trifluoromethane-sulfonyloxy), halo-sulfonyloxy (e.g. fluorosulfonyloxy), halonium, diarylsulfo-nylamino (e.g. ditosyl), quaternary ammonium $C_{1-4}$ alkylsulfonyloxy, $C_{1-4}$ perfluoroalkanoyloxy (e.g. trifluoroacetyloxy), $C_{1-4}$ alkanoyloxy (e.g. acetyloxy), aroyloxy (e.g. benzoyloxy), diazonium, oxonium or perchloryloxy groups.

More preferred values of $L^2$ include a different lower alkoxy group to that which is to be replaced by the group $R^3O$ (e.g. methoxy, provided that $R^3$ does not represent methyl) and, especially, halo (including bromo and, particularly, chloro).

The skilled person will appreciate that compounds that may serve to provide the group $R^3O$ include lower alkoxides of alkali metals (e.g. lithium, sodium, potassium), or of alkaline earth metals (e.g. magnesium, calcium). Preferred alkoxides include those of sodium and potassium.

Alternatively, the $R^3O^-$ anion may be produced in situ by reaction of the relevant lower alkyl alcohol (or an alkali/alkaline earth metal alkoxide) with an auxiliary base, which should not compete with the relevant $R^3O^-$ group in the nucleophilic substitution of $L^2$ by being suitably sterically hindered. In this respect, suitable auxiliary bases may include a sterically hindered alkoxide or a secondary or tertiary amine.

Compounds of formula IX may be prepared by reaction of a compound of formula X,

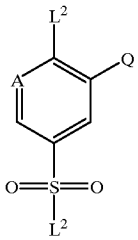

wherein A, Q and $L^2$ are as hereinbefore defined with a compound of formula VII as hereinbefore defined, for example as described hereinbefore.

Compounds of formula X may be prepared by known techniques. For example compounds of formula X in which both $L^2$ groups represent halo (e.g. chloro) may be prepared by reaction of a corresponding compound of formula XI, wherein A and Q are as hereinbefore defined, with a suitable halogenating agent (e.g. thionyl chloride), for example at around 80 to 100° C., optionally in the presence of a suitable solvent (e.g. dimethylformamide) and/or (optionally) an appropriate activating agent (e.g. dimethylformamide). The skilled person will appreciate that when an activating agent and a solvent are both employed, they may be either the same or different compounds.

Compounds of formula XI may be prepared by techniques known to those skilled in the art. For example, compounds of formula XI may be prepared by reacting a corresponding compound of formula XII, wherein A and Q are as hereinbefore defined, with a sulfonating agent (e.g. oleum) under conditions known to those skilled in the art.

(c) Compounds of formula IV in which G represents —CN may alternatively be prepared by dehydration of a corresponding compound of formula IV in which G represents —C(O)NH$_2$, under appropriate reaction conditions, for example at low temperature (e.g. at between −5° C. and room temperature (preferably at around 0° C.)) in the presence of a suitable dehydrating agent (for example: $P_2O_5$; POCl$_3$; PCl$_5$; CCl$_4$ and triphenylphosphine; trifluoroacetic anhydride and a suitable base (e.g. triethylamine or pyridine); or SOCl$_2$) and an appropriate organic solvent (e.g. dichloromethane, toluene, chlorobenzene or heptane).

(d) Compounds of formula IV in which G represents —C(O)NH$_2$ may be prepared from a corresponding compound of formula IV in which G represents —C(O)

OH, for example by reaction with ammonia or a derivative thereof (e.g. ammonium acetate). The skilled person will appreciate that this reaction may preferably be carried out in the presence of an appropriate activating reagent (e.g. N,N'-carbonyldiimidazole), in an appropriate solvent, e.g. ethyl acetate, dichloromethane or butan-2-one, resulting in the formation of an intermediate imidazolide (which may be isolated if desired), followed by reaction with e.g. ammonium acetate at between room and reflux temperature. Those skilled in the art will also appreciate that the activation of benzoic acid derivatives may also be accomplished with many other activating agents, for example as described in J. March, *Advanced Organic Chemistry*, 3$^{rd}$ Edition, Chapter 10, 371–374, John Wiley & Sons (1985).

(e) Compounds of formula IV in which G represents —C(O)OH may be prepared by known techniques. For example, such compounds may be prepared according to, or by analogy with, methods described in European patent application EP 812 845 (the disclosures in which document are hereby incorporated by reference). Compounds of formula IV in which G represents —C(O)OH may alternatively be prepared by reaction of a corresponding compound of formula XIII, wherein A and L$^2$ are as hereinbefore defined, with a compound that with provide the group R$^3$O, for example under conditions as described hereinbefore for the preparation of compounds of formula IV.

Compounds of formula XIII may be prepared by known techniques, for example, according to, or by analogy with procedures described hereinbefore for the preparation of compounds of formula IX.

Other compounds of formula IV may be prepared from appropriate starting materials (which include inter alia compounds of formula IV), using techniques known to those skilled in the art and/or according to, or by analogy with procedures described hereinbefore for the preparation of compounds of formula II.

Compounds of formula IIIA, IIIB, VA, VB, VC, VD, VE, VF, VII, VIII, XII, and derivatives thereof, when not commercially available or not subsequently described, may be obtained either by analogy with processes described herein, or by conventional synthetic procedures, in accordance with standard techniques, from readily available starting materials using appropriate reagents and reaction conditions.

Compounds may be isolated from reaction mixtures using known techniques.

Substituents on the aryl (e.g. phenyl), and (if appropriate) heterocyclic, group(s) in compounds defined herein may be converted to other substituents using techniques well known to those skilled in the art. For example, amino may be converted to amido, amido may be hydrolysed to amino, hydroxy may be converted to alkoxy, alkoxy may be hydrolysed to hydroxy etc.

It will be appreciated by those skilled in the art that, in the processes described above, the functional groups of intermediate compounds may be, or may need to be, protected by protecting groups.

Functional groups which it is desirable to protect thus include hydroxy, amino and carboxylic acid. Suitable pro tecting groups for hydroxy include trialkylsilyl and diaryalkylsilyl groups (e.g. tert-butyldimethylsilyl, tert-butyldiphenylsilyl or trimethylsilyl), tetrahydropyranyl, benzyl and alkylcarbonyl groups (e.g. methyl- and ethylcarbonyl groups). Suitable protecting groups for amino include benzyl, tert-butyloxycarbonyl, 9-fluorenylmethoxycarbonyl or benzyloxycarbonyl. Suitable protecting groups for carboxylic acid include C$_{1-6}$ alkyl, allyl or benzyl esters.

The protection and deprotection of functional groups may take place before or after any of the reaction steps described hereinbefore.

Protecting groups may be removed in accordance with techniques which are well known to those skilled in the art and as described hereinafter.

The use of protecting groups is fully described in "Protective Groups in Organic Chemistry", edited by J W F McOmie, Plenum Press (1973), and "Protective Groups in Organic Synthesis", 3$^{rd}$ edition, T W Greene & P G M Wutz, Wiley-Interscience (1999).

Persons skilled in the art will appreciate that, in order to obtain compounds of the formula II in an alternative, and, on some occasions, more convenient, manner, the individual process steps mentioned herein may be performed in a different order, and/or the individual reactions may be performed at a different stage in the overall route (i.e. substituents may be added to and/or chemical transformations performed upon, different intermediates to those associated hereinbefore with a particular reaction). This will depend inter alia on factors such as the nature of other functional groups present in a particular substrate, the availability of key intermediates and the protecting group strategy (if any) to be adopted. Clearly, the type of chemistry involved will influence the choice of reagent that is used in the said synthetic steps, the need, and type, of protecting groups that are employed, and the sequence for accomplishing the synthesis.

Certain intermediates that are employed in the processes described herein are novel. According to the invention there is further provided: (a) compounds of formulae II as defined hereinbefore; and (b) compounds of formula IV as defined hereinbefore. Preferred compounds of formula II include those in which, when A represents CH, then R$^x$ does not represent —NH$_2$.

According to a further aspect of the invention there is provided compounds of formula II, as defined hereinbefore, in which R$^x$ represents —SR$^d$, —SH and —OR$^e$ (wherein R$^d$ and R$^e$ are as hereinbefore defined).

The process of the invention may have the advantage that sildenafil and analogues thereof may be prepared from commercially-available starting materials in fewer steps than in processes described in the prior art, without concomitant losses in terms of yield of key intermediates and of final products.

Further, the process of the invention may have the advantage that sildenafil and analogues thereof may be prepared in less time, more conveniently, and at a lower cost, than when prepared in processes described in the prior art.

The invention is illustrated, but in no way limited, by the following examples.

All $^1$H NMR spectra were recorded using a Varian Unity 300 MHz machine.

EXAMPLE 1

5-[2-Ethoxy-5-(4-methylpiperazin-1-ylsulfonyl) phenyl]-1-methyl-3-n-propyl-1,6-dihydro-7H-pyrazolo[4,3-d]pyrimidin-7-one, sildenafil

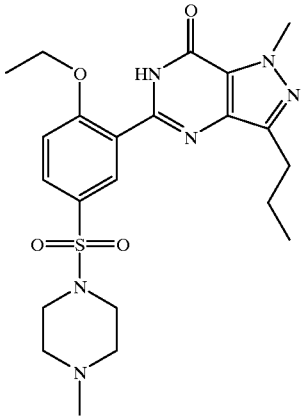

A solution of ethyl 2-ethoxy-5-(4-methyl-1-piperazinylsulfonyl)-benzimidate (2.2 g, 6.2 mmol, from step 1(c) below) and 4-amino-1-methyl-3-propyl-1H-pyrazole-5-carboxamide (Example 37 of EP 0463756) (17 mL of a 10% w/v solution in ethyl acetate, 6.8 mmol) in xylene (40 mL) was heated to reflux. Approximately 10 mL of the solvent was distilled to remove the ethyl acetate. The reaction started to foam at 129° C. and gave off ammonia gas. The temperature gradually rose to 136° C. over three days and the foaming ceased. When the reaction was complete, the solvent was removed to give a brown oil which was further purified using medium pressure column chromatography (DCM and methanol as eluents), giving the title product in 76% yield, along with recovered 4-amino-1-methyl-3-propyl-1H-pyrazole-5-carboxamine (22.6%). The yield based upon unrecovered 4-amino-1-methyl-3-propyl-1H-pyrazole-5-carboxamide was 85%. The product was recrystallised from methyl ethyl ketone (MEK) to give material for analysis.

mp 184–185° C.
$^1$H NMR (CDCl$_3$) δ1.03 (3H, t), 1.62 (3H, t), 1.85 (2H, m), 2.22 (3H, s), 2.49 (4H, m), 2.94 (2H, t), 3.11 (4H, m), 4.27 (3H, s), 4.38 (2H, q), 7.17 (1H, d), 7.83 (1H, d), 8.81 (1H, s)
m/z found 475 [M+H]$^+$ 100%, C$_{22}$H$_{31}$N$_6$O$_4$S requires 475

Preparative Examples for Example 1
1(a) 5-Chlorosulfonyl-2-ethoxybenzonitrile
(Compound of formula VI where A=CH; R$^3$=Et; G=CN; L=Cl)

Commercially available 2-ethoxybenzonitrile (1.0 g, 0.007 mol) was added to an ice-cold solution of chlorosulfonic acid (1.9 mL, 0.03 mol) and thionyl chloride (0.5 mL, 0.007 mol) over 30 minutes, left to stir overnight, quenched by pouring onto ice/water (20 mL), and granulated for 30 minutes. The precipitated product was filtered off, washed with water and dried on the filter under nitrogen to give 1.0 g (59%) of the sub-title compound as a yellow solid, which was used directly in the next step.

$^1$H NMR (CDCl$_3$) δ1.54 (3H, t), 4.31 (2H, m), 7.16 (1H, d), 8.18 (1H, d), 8.12 (1H, s)
1(b) 2-Ethoxy-5-(4-methyl-1-piperazinylsulfonyl) benzonitrile (compound of formula IV where A=CH; R$^3$=Et; G=CN; R$^4$=Me) 5-Chlorosulfonyl-2-ethoxybenzonitrile (1.0 g, 0.004 mol, from step 1(a) above) was dissolved in dichloromethane (DCM; 6 mL) and cooled to between 0 and 5° C. N-Methylpiperazine (0.8 mL, 0.0091 mol) was added dropwise over 30 minutes and the solution left to stir overnight. The solution was diluted with 10 mL of water and the product extracted with dichloromethane. The solvent was removed in vacuo to give the sub-title compound as a yellow oil (0.8 g, 66.6%).

$^1$H NMR (CDCl$_3$) δ1.54 (3H, t), 2.2 (3H, s), 2.45 (4H, m), 2.97 (4H, m), 4.18 (2H, q), 7.07 (1H, d), 7.84 (1H, d), 7.90(1H, s)
m/z found 310 [M+H$^+$] 75%, C$_{14}$H$_{19}$N$_3$O$_3$S requires 310
1(c) Ethyl 2-ethoxy-5-(4-methyl-1-piperazinylsulfonyl) benzimidate (compound of formula II where A=CH; R$^3$=Et; R$^4$=Me)

A suspension of 2-ethoxy-5-(4-methyl-1-piperazinylsulfonyl)benzonitrile (2.6 g, 8.4 mmol, from step 1(b) above) in ethanol (80 mL) was cooled to 0° C. HCl gas was slowly bubbled through the resultant until saturation. After standing for 3 days, the reaction was complete and ethanol was removed in vacuo. The crude solid was dissolved in DCM and washed with aqueous sodium bicarbonate solution. The solvent was removed to give the sub-title compound as a brown solid (48%).

mp 158–160° C.
$^1$H NMR (CDCl$_3$) δ1.39 (3H, t), 1.56 (3H, t), 2.53 (3H, s), 2.89 (4H, m), 3.32 (4H, m), 4.14 (2H, q), 4.37 (2H, q), 7.08 (1H, d), 7.74 (1H, d), 8.15 (1H, s)
m/z found 357 [M+H]$^+$ 25%, C$_{16}$H$_{26}$N$_3$O$_4$S requires 357
1(d) Alternative Synthesis of 2-Ethoxy-5-(4-methyl-1-piperazinylsulfonyl)-benzonitrile—the compound of Step 1(b) above
1(d)(i) 2-Ethoxy-5-(4-methyl-1-piperazinylsulfonyl) benzamide (compound of formula II where A=CH; R$^3$=Et; G=C(O)NH$_2$; R$^4$=Me)

To a slurry of 2-ethoxy-5-(4-methyl-1-piperazinylsulfonyl)benzoic acid (50 g, 0.15 mol, see EP 812 845) in EtOAc (250 mL), was added N,N'-carbonyldiimidazole (CDI; 27 g, 0.166 mol) in one portion. The slurry was heated to about 40° C., upon which the reaction commenced. After the CDI had reacted, the reaction was heated to reflux for 4 hours. Ammonium acetate (40 g, 0.5 mol) was added to the slurry, and the resultant was left to reflux overnight. After cooling the resultant slurry was filtered to give the sub-title product as a fine white solid (40.7 g, 83%).

mp 185–189° C.
$^1$H NMR (CDCl$_3$) δ1.58 (3H, t), 2.29 (3H, s), 2.47 (4H, m), 3.06 (4H, m), 4.29 (2H, q), 6.13 (1H, s), 7.12 (1H, d), 7.70 (1H, s), 7.82 (1H, d), 8.60 (1H, s)
m/z found 328 [M+H$^+$] 100%, C$_{14}$H$_{22}$N$_3$O$_4$S requires 328
1(d)(ii) 2-Ethoxy-5-(4-methyl-1-piperazinylsulfonyl) benzonitrile (compound of formula II where A=CH; R$^3$=Et; G=CN; R$^4$=Me)

To an ice cold suspension of 2-ethoxy-5-(4-methyl-1-piperazinylsulfonyl)benzamide (32 g, 0.098 mol, from step 1(d)(i) above) and triethylamine (56 mL, 0.38 mol) in DCM was added trifluoroacetic anhydride (34.4 mL, 0.22 mol) which resulted in a brown solution. This was allowed to stir overnight and was quenched with water (100 mL). The organic layer was washed with water (2×100 mL) and brine (50 mL) and the DCM was removed in vacuo to give 56.8 g of brown oil which was recrystallised from ethyl acetate to give the product as a brown solid (18.7 g, 61.7%).

mp 119–120° C.
$^1$H NMR (CDCl$_3$) δ1.54 (3H, t), 2.2 (3H, s), 2.45 (4H, m), 2.97 (4H, m), 4.18 (2H, q), 7.07 (1H, d), 7.84 (1H, d), 7.90(1H, s)
m/z found 310 [M+H$^+$] 75%, C$_{14}$H$_{19}$N$_3$O$_3$S requires 310

The product of Preparative example 1(d) may be used to prepare compounds of formula II, and of formula I, in which $R^3$ is ethyl and $R^4$ is methyl, by employing similar procedures to those described in Example 1, and in the preparative Example step 1(c).

EXAMPLE 2

Alternative Synthesis of (5-[2-ethoxy-5-(4-methylpiperazin-1-ylsulfonyl)phenyl]-1-methyl-3-n-propyl-1,6-dihydro-7H-pyrazolo[4,3-d]pyrimidin-7-one), Sildenafil

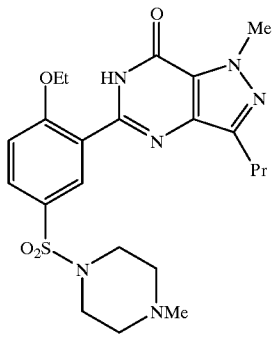

4-Amino-1-methyl-3-n-propyl-1H-pyrazole-5-carboxylate (prepared according to Example 37 of EP-0463756) (0.182 g, 1.0 mMol) and 2-ethoxy-5-(4-methyl-1-piperazinylsulfonyl)benzamidine (the compound of Preparation 5 hereinafter) (0.326 g, 1.0 mMol) were stirred in xylene (15 mL) and this mixture was heated to reflux for 9 h. After evaporation and re-evaporation from toluene the residue was subjected to chromatography on silica gel eluting with ethyl acetate/methanol mixtures to give the desired product, 0.033 g. M/Z=475 (M+H); 1H NMR (300 MHz, CDCl3); 1.04 (t, 3H), 1.66 (t, 3H), 1.88 (sextet, 2H), 2.29 (s, 3H), 2.51 (m, 4H), 2.95 (t, 3H), 3.13 (m, 4H), 4.29 (s, 3H), 4.39 (quart. 2H), 7.16 (d, 1H), 7.85 (dd, 1H), 8.85 (d, 1H).

According to a preferred process according to the present invention there is provided a process for the preparation of sildenafil substantially as described in Examples 1 and 2 herein before and Preparations for Example 1 herein before.

According to another preferred process compounds wherein $G=CO_2Et$ can be prepared via the telescoped chemistry of Preparation 2 as detailed hereinafter.

Example 3 illustrates how one of the preferred compounds noted herein can be made. The present invention provides an alternative method for the preparation of the compound of Example 3 by using any of the routes hereinbefore detailed and especially as described in Examples 1 and 2.

EXAMPLE 3

2-(Methoxyethyl)-5-[2-ethoxy-5-(4-ethylpiperazin-1-ylsulphonyl)pyridin-3-yl]-3-ethyl-2,6-dihydro-7H-pyrazolo[4,3-d]pyrimidin-7-one

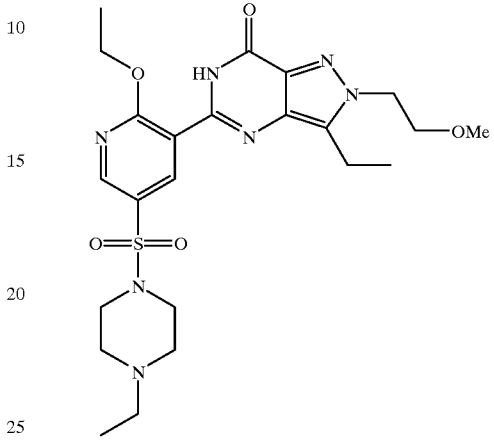

A mixture of the product from step 3(j) below (0.75 mmol), potassium bis(trimethylsilyl)amide (298 mg, 1.50 mmol) and ethyl acetate (73 microliters, 0.75 mmol) in ethanol (10 ml) was heated at 120° C. in a sealed vessel for 12 hours. The cooled mixture was partitioned between ethyl acetate and aqueous sodium bicarbonate solution, and the layers separated. The organic phase was dried (MgSO$_4$), and evaporated under reduced pressure. The crude product was purified by column chromatography on silica gel using dichloromethane:methanol (98:2) as eluant to afford the title compound, 164 mg; Found: C, 53.18; H, 6.48; N, 18.14; $C_{23}H_{33}N_7O_5S;0.20C_2H_5CO_2CH_3$ requires C, 53.21; H, 6.49; N, 18.25%; δ(CDCl$_3$): 1.04 (3H, t), 1.40 (3H, t), 1.58 (3H, t), 2.41 (2H, q), 2.57 (4H, m), 3.08 (2H, q), 3.14 (4H, m), 3.30 (3H, s), 3.92 (2H, t), 4.46 (2H, t), 4.75 (2H, q), 8.62 (1H, d), 9.04 (1H, d), 10.61 (1H, s); LRMS: m/z 520 (M+1)$^+$; mp 161–162° C.

Preparation of Starting Materials for Example 3

3(a) Pyridine-2-amino-5-sulphonic acid

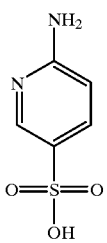

2-Aminopyridine (80 g, 0.85 mol) was added portionwise over 30 minutes to oleum (320 g) and the resulting solution heated at 140° C. for 4 hours. On cooling, the reaction was poured onto ice (200 g) and the mixture stirred in an ice/salt bath for a further 2 hours. The resulting suspension was filtered, the solid washed with ice water (200 ml) and cold IMS (200 ml) and dried under suction to afford the sub-title compound as a solid, 111.3 g; LRMS: m/z 175 (M+1)⁺.

3(b) Pyridine-2-amino-3-bromo-5-sulphonic acid

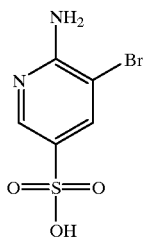

Bromine (99 g, 0.62 mol) was added dropwise over an hour, to a hot solution of the product from step 3(a) (108 g, 0.62 mol) in water (600 ml) so as to maintain a steady reflux. Once the addition was complete the reaction was cooled and the resulting mixture filtered. The solid was washed with water and dried under suction to afford the sub-title compound, 53.4 g; δ(DMSOd₆, 300 MHz): 8.08 (1H, s), 8.14 (1H, s); LRMS : m/z 253 (M)⁺.

3(c) Pyridine-3-bromo-2-chloro-5-sulphonyl chloride

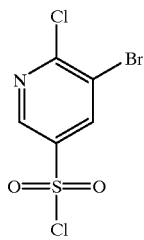

A solution of sodium nitrite (7.6 g, 110.0 mmol) in water (30 ml) was added dropwise to an ice-cooled solution of the product from step 3(b) (25.3 g, 100.0 mmol) in aqueous hydrochloric acid (115 ml, 20%), so as to maintain the temperature below 6° C. The reaction was stirred for 30 minutes at 0° C. and for a further hour at room temperature. The reaction mixture was evaporated under reduced pressure and the residue dried under vacuum at 70° C. for 72 hours. A mixture of this solid, phosphorus pentachloride (30.0 g, 144 mmol) and phosphorus oxychloride (1 ml, 10.8 mmol) was heated at 125° C. for 3 hours, and then cooled. The reaction mixture was poured onto ice (100 g) and the resulting solid filtered, and washed with water. The product was dissolved in dichloromethane, dried (MgSO₄), and evaporated under reduced pressure to afford the sub-title compound as a yellow solid, 26.58 g; δ(CDCl₃, 300 MHz): 8.46 (1H, s), 8.92 (1H, s).

3(d) 3-Bromo-2-chloro-5-(4-ethylpiperazin-1-ylsulphonyl)pyridine

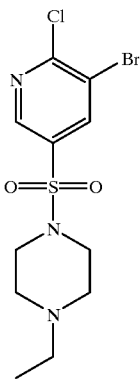

A solution of 1-ethylpiperazine (11.3 ml, 89.0 mmol) and triethylamine (12.5 ml, 89.0 mmol) in dichloromethane (150 ml) was added dropwise to an ice-cooled solution of the product from step 3(c) (23.0 g, 79.0 mmol) in dichloromethane (150 ml) and the reaction stirred at 0° C. for an hour. The reaction mixture was concentrated under reduced pressure and the residual brown oil was purified by column chromatography on silica gel, using an elution gradient of dichloromethane:methanol (99:1 to 97:3) to afford the sub-title compound as an orange solid, 14.5 g; δ(CDCl₃, 300 MHz): 1.05 (3H, t), 2.42 (2H, q), 2.55 (4H, m), 3.12 (4H, m), 8.24 (1H, s), 8.67 (1H, s)

3(e) 3-Bromo-2-ethoxy-5-(4-ethylpiperazin-1-ylsulphonyl)pyridine

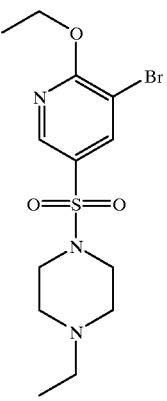

A mixture of the product from stage 3(d) (6.60 g, 17.9 mmol) and sodium ethoxide (6.09 g, 89.55 mmol) in ethanol (100 ml) was heated under reflux for 18 hours, then cooled. The reaction mixture was concentrated under reduced pressure, the residue partitioned between water (100 ml) and ethyl acetate (100 ml), and the layers separated. The aqueous phase was extracted with ethyl acetate (2×100 ml), the combined organic solutions dried (MgSO₄) and evaporated under reduced pressure to afford the sub-title compound as a brown solid, 6.41 g; Found: C, 41.27; H, 5.33; N, 11.11. $C_{13}H_{20}BrN_3O_3S$ requires C, 41.35; H, 5.28; N, 10.99%; δ(CDCl₃, 300 MHz): 1.06 (3H, t), 1.48 (3H, t), 2.42 (2H, q), 2.56 (4H, m), 3.09 (4H, m), 4.54 (2H, q), 8.10 (1H, s), 8.46 (1H, s); LRMS: m/z 378, 380 (M+1)⁺.

3(f) Pyridine 2-ethoxy-5-(4-ethylpiperazin-1-ylsulphonyl)-3-carboxylic acid ethyl ester

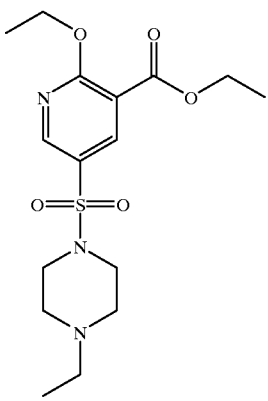

A mixture of the product from stage 3(e) (6.40 g, 16.92 mmol), triethylamine (12 ml, 86.1 mmol), and palladium (0) tris(triphenylphosphine) in ethanol (60 ml) was heated at 100° C. and 200 psi, under a carbon monoxide atmosphere, for 18 hours, then cooled. The reaction mixture was evaporated under reduced pressure and the residue purified by column chromatography on silica gel, using an elution gradient of dichloromethane:methanol (100:0 to 97:3) to afford the sub-title compound as an orange oil, 6.2 g; δ(CDCl$_3$, 300 MHz) 1.02 (3H, t), 1.39 (3H, t), 1.45 (3H, t), 2.40 (2H, q), 2.54 (4H, m), 3.08 (4H, m), 4.38 (2H, q), 4.55 (2H, q), 8.37 (1H, s), 8.62 (1H, s); LRMS: m/z 372 (M+1)$^+$.

3(g) Pyridine 2-ethoxy-5-(4-ethylpiperazin-1-ylsulphonyl)-3-carboxylic acid

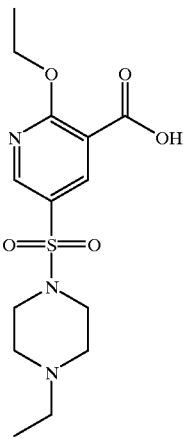

A mixture of the product from stage 3(f) (4.96 g, 13.35 mmol) and aqueous sodium hydroxide solution (25 ml, 2N, 50.0 mmol) in ethanol (25 ml) was stirred at room temperature for 2 hours. The reaction mixture was concentrated under reduced pressure to half it's volume, washed with ether and acidified to pH 5 using 4N hydrochloric acid. The aqueous solution was extracted with dichloromethane (3×30 ml), the combined organic extracts dried (MgSO$_4$) and evaporated under reduced pressure to afford the sub-title compound as a tan colored solid, 4.02 g; δ(DMSOd$_6$, 300 MHz): 1.18 (3H, t), 1.37 (3H, t), 3.08 (2H, q), 3.17–3.35 (8H, m), 4.52 (2H, q), 8.30 (1H, s), 8.70 (1H, s).

3(h) 4-[2-Ethoxy-5-(4-ethylpiperazin-1-ylsulphonyl)pyridin-3-ylcarboxamido]-1H-3-ethylpyrazole-5-carboxamide

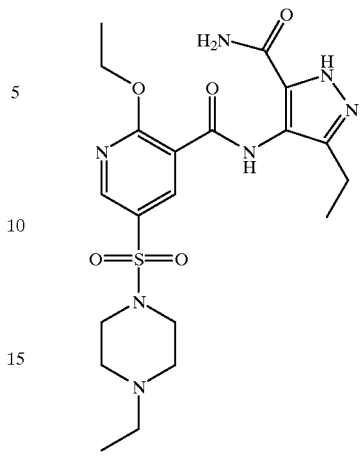

A solution of 4-amino-3-ethyl-1H-pyrazole-5-carboxamide (WO 9849166, preparation 8) (9.2 g, 59.8 mmol) in N,N-dimethylformamide (60 ml) was added to a solution of the product from stage g) (21.7 g, 62.9 mmol), 1-hydroxybenzotriazole hydrate (10.1 g, 66.0 mmol) and triethylamine (13.15 ml, 94.3 mmol) in dichloromethane (240 ml). 1-(3-Dimethylaminopropyl)-3-ethylcarbodiimide hydrochloride (13.26 g, 69.2 mmol) was added and the reaction stirred at room temperature for 6 hours. The dichloromethane was removed under reduced pressure, the remaining solution poured into ethyl acetate (400 ml), and this mixture washed with aqueous sodium bicarbonate solution (400 ml). The resulting crystalline precipitate was filtered, washed with ethyl acetate and dried under vacuum, to afford the sub-title compound, as a white powder, 22 g; δ(CDCl$_3$+1 drop DMSOd$_6$) 0.96 (3H, t), 1.18 (3H, t), 1.50 (3H, t), 2.25–2.56 (6H, m), 2.84 (2H, q), 3.00 (4H, m), 4.70 (2H, q), 5.60 (1H, br s), 6.78 (1H, br s), 8.56 (1H, d), 8.76 (1H, d), 10.59 (1H, s), 12.10–12.30 (1H, s); LRMS: m/z 480 (M+1)$^+$.

3(i) 2-Methoxyethyl-4-[2-ethoxy-5-(4-ethylpiperazin-1-ylsulphonyl)pyridin-3-ylcarboxamido]-3-ethylpyrazole-5-carboxamide

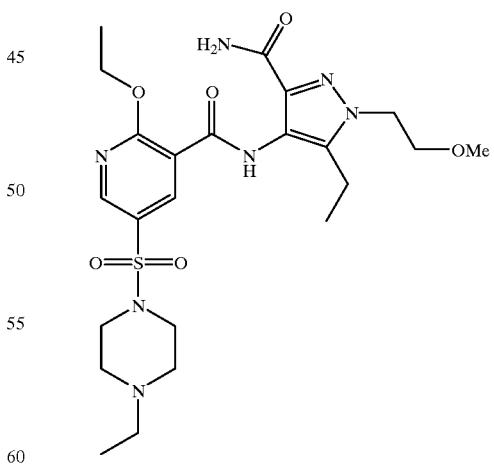

1-Bromo-2-methoxyethane (1.72 mmol) was added to a solution of the product from stage 3(h) (750 mg, 1.56 mmol) and caesium carbonate (1.12 g, 3.44 mmol) in N,N-dimethylformamide (15 ml) and the reaction stirred at 60° C. for 18 hours. The cooled mixture was partitioned between water and ethyl acetate, and the layers separated. The organic layer was dried ($MgSO_4$), concentrated under reduced pressure and azeotroped with toluene to give a solid. This product was recrystallised from ether, to afford the sub-title compound as a white solid.

δ($CDCl_3$): 1.04 (3H, t), 1.22 (3H, t), 1.60 (3H, t), 2.44 (2H, q), 2.54 (4H,m), 2.96 (2H, q), 3.12 (4H, m), 3.36 (3H, s), 3.81 (2H, t), 4.27 (2H, t), 4.80(2H, q), 5.35(1H, s), 6.68 (1H, s), 8.66 (1H, d), 8.86 (1H, d), 10.51 (1H, s).

General Preparative Examples

Preparation 1

2-Ethyl-2-ethoxy-5-(4-ethyl-1-piperazinylsulfonyl) pyridinoate—Compound IV wherein $R^3$ & $R^4$=Et; A=N; G=$CO_2$H Preparation (1a) 2-Hydroxy-5-sulfonicotinic acid 2-Hydroxynicotinic acid (27 Kg, 194.2 mol) was added portionwise to 30% oleum (58.1 Kg) at 50° C. over 1 hr. This caused an exotherm to 82° C. The reaction mixture was heated further to 140° C. After maintaining this temperature for 12 hrs the reactor contents were cooled to 15 C. and filtered. The filter cake was then re-slurried with acetone (33 Kg) at room temperature, filtered and dried to afford the sub-title compound (35.3 Kg, 83%) as a white solid. Decomposition pt 273° C. δ($DMSO_{d6}$): 7.93 (1H, d), 8.42 (1H, d). m/z (Found:220 [M+H]$^+$, 100%. $C_6H_6NO_6S$ requires 220.17).

Preparation (1b) Ethyl 2-hydroxy-5-sulfonicotinoate

2-Hydroxy-5-sulfonicotinic acid (500 g, 2.28 mol) was dissolved in ethanol (2.5 L) with stirring and heated to 80° C. After 30 mins 0.5 L of solvent was distilled off, then replaced with fresh ethanol (0.5 L) and taken back to 80° C. After a further 60 mins 1.0 L of solvent was distilled off, then replaced with fresh ethanol (1.0 L) and taken back to 80° C. After a further 60 mins 1.0 L of solvent was distilled off, the reaction cooled to 22° C. and stirred for 16 hr.

The precipitated product was filtered, washed with ethanol (0.5 L) and dried at 50° C. under vacuum to afford the sub-title compound (416 g, 74%) as a white solid. Decomposition pt 237° C. δ($DMSO_{d6}$): 1.25 (3H, t), 4.19 (2H, q), 7.66 (1H, d), 8.13 (1H, d). m/z (Found:248 [M+H]$^+$, 100%. $C_8H_{10}NO_6S$ requires 248.22).

Preparation (1c) Ethyl 2-chloro-5-chlorosulfonicotinoate

Ethyl 2-hydroxy-5-sulfonicotinoate (24.7 g, 0.1 mol) was slurried in thionyl chloride (238 g, 2.0 mol) and dimethylformamide (1.0 mL) with stirring. The reaction mixture was then heated to reflux for 2.5 hr. The bulk of the thionyl chloride was removed under vacuum with residual thionyl chloride removed with a toluene azeotrope to afford the crude sub-title compound (30.7 g, 108%) as a yellow oil. δ($CDCl_3$): 1.46 (3H, t), 4.50 (2H, q), 8.72 (1H, d), 9.09 (1H, d). This was taken directly onto the next step.

Preparation (1d)Ethyl 2-chloro-5-(4-ethyl-1-piperazinylsulfonyl) nicotinoate

Crude ethyl 2-chloro-5-chlorosulfonicotinoate (30.7 g, 0.1 mol assumed) was dissolved in ethyl acetate (150 mL) with stirring then ice cooled. To this was added a solution of N-ethylpiperazine (11.4 g, 0.1 mol) and triethylamine (22.5 g, 0.22 mol) in ethyl acetate (SOL), carefully over 30 mins, keeping the internal temperature below 10° C. Once the addition was complete the reaction was allowed to warm to 22° C. and stir for 1 hr. The solid was filtered off and the remaining filtrate was concentrated under vacuum to afford the crude sub-title compound (37.1 g, 103%) as a crude yellow gum. δ($CDCl_3$): 1.10 (3H, t), 1.42 (3H, m), 2.50 (2H, m), 2.60 (4H, m), 3.19 (4H, m), 4.43 (2H, q), 8.40 (1H, d), 8.80 (1H, d). m/z (Found:362 [M+H]$^+$, 100%. $C_{14}H_{21}ClN_3O_4S$ requires 362.85).

Preparation (1e)Ethyl 2-ethoxy-5-(4-ethyl-1-piperazinylsulfonyl)nicotinoate

A solution of ethyl 2-chloro-5-(4-ethyl-1-piperazinylsulfonyl)nicotinoate (36.1 g, 0.1 mol) in ethanol (180 mL) was cooled to 10° C. with stirring. Sodium ethoxide (10.2 g, 0.15 mol) was added portionwise keeping the temperature below 20° C. The reaction mixture was then stirred at ambient temperature for 18 hours. The precipitate was filtered off and water (180 mL) added to the filtrate. The filtrate was then heated to 40° C. for 1 hour. Ethanol (180 mL) was then distilled off at ambient pressure and the remaining aqueous solution allowed to cool to ambient temperature. The precipitated product was then filtered off, washed with water and dried under vacuo at 50° C. to afford the sub-title compound (12.6 g, 34%) as a light brown solid. M.p. 66–68° C. δ($CDCl_3$): 1.04 (3H, t), 1.39 (3H, t), 1.45 (3H, t), 2.41 (2H, q), 2.52 (4H, m), 3.08 (4H, m), 4.38 (2H, q), 2.57 (2H, q) 8.38 (1H, d), 8.61 (1H, d). m/z (Found: 372 [M+H]$^+$, 100%. $C_{16}H_{26}N_3O_5S$ requires 372.46).

Preparation (1f) 2-Ethoxy-5-(4-ethyl-1-piperazinylsulfonyl) nicotinic acid

Ethyl 2-ethoxy-5-(4-ethyl-1-piperazinylsulfonyl) nicotinoate (10.2 g, 0.0275 mol) was dissolved in toluene (50 mL) and a solution of sodium hydroxide (1.1 g, 0.0275 mol) in water (20 mL) added to it. This two phase mixture was then stirred vigorously at ambient temperature overnight. The aqueous phase was separated off and adjusted to pH=5.6 by addition of conc. hydrochloric acid. The precipitated product was slurried with ice cooling for 15 minutes, filtered, water washed and dried under vacuo at 50° C. to afford the sub-title compound (4.1 g, 43%) as an off-white solid. Mpt 206–207° C. δ($CDCl_3$): 1.25 (3H, t), 1.39 (3H, t), (2H, q), 3.03 (4H, m), 3.25 (4H, m), 4.50 (2H, q), 8.25 (1H, d), 8.56 (1H, d). m/z (Found:344 [M+H]$^+$, 100%. $C_{14}H_{22}N_3O_5S$ requires 344.38).

This step is a simple hydrolysis and the yield of 43% is not optimum. The same hydrolysis was carried out in preparation 23 of PCT/IB99/00519 (which is incorporated herein by reference) and a more optimised yield of 88% was obtained for the hydrolysis.

Preparation (1 g) Alternative Preparation for 2-Ethoxy-5-(4-ethyl-1-piperazinylsulfonyl)nicotinic acid (the compound of Preparation (1f)-Telescoped process in toluene from ethyl 2-hydroxy-5-sulfonicotinoate Ethyl 2-hydroxy-5-sulfonicotinoate (the compound of Preparation (1b)) (441.5 g, 1.79 mol) was dissolved in toluene (1.77 L) and thionyl chloride (1.06 Kg, 8.93 mol) and dimethylformamide (71.3 mL) were then added. The stirred suspension was then heated to reflux for 3 hours to yield a yellow solution. Thionyl chloride (2.87 L) was then distilled with continual replacement with toluene (2.15 L). The pale yellow solution was then cooled to 10° C. and a stirred solution of N-ethylpiperazine (198.9 g, 1.66 mol) and triethylamine (392.2 g, 3.88 mol) in toluene (700 mL) added dropwise over 90 minutes keeping the reaction mixture below 10° C. The reaction was stirred at ambient temperature for 18 hours then washed with water (2×700 mL) and brine (2×350 mL). The toluene phase was azeotropically dried by distilling off 1750 mL which was continuously replaced by dry toluene (1750 mL). The remaining brown solution was cooled to 10° C. and sodium ethoxide (178.0 g, 2.62 mol) was added portionwise keeping the temperature below 10° C. The reaction was then stirred at 10° C. for 1 hour then allowed to warm to ambient temperature and stirred for 18 hours. Sodium hydroxide (34.9 g, *mol) dissolved in water (1.5 L) was then added to the toluene mixture and the 2 phase mixture was vigorously stirred for 18 hours at 40° C. Once cooled to ambient temperature the aqueous phase was separated off. To this was added conc. hydrochloric acid to pH=3 which precipitated a light brown solid which was granulated for 2 hour with ice cooling. The precipitate was filtered washed with water (300 mL) and dried under vacuo at 50° C. to afford the sub-title compound (338.4 g, 57.4%) as an off-white solid. Mpt 206–207° C. δ(CDCl₃): 1.25 (3H, t), 1.39 (3H, t), 2.82 (2H, q), 3.03 (4H, m), 3.25 (4H, m), 4.50 (2H, q), 8.25 (1H, d), 8.56 (1H, d). m/z (Found:344 [M+H]⁺, 100%. $C_{14}H_{22}N_3O_5S$ requires 344.38).

Preparation 2

2-ethoxy-5-(4-methyl-1-piperazinylsulfonyl) benzonitrile

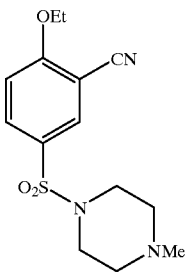

Triethylamine (49.1 g, 0.485 Mol) was added to a slurry of 2-ethoxy-5-(4-methyl-1-piperazinylsulfonyl)benzamide (40.9 g, 0.125 Mol) in dichloromethane (200 mL) and this mixture was cooled to 0° C. Trifluoroacetic anhydride (58.9 g, 0.28 Mol) was added dropwise over 45 min and was washed in with DCM (25 mL) before the reaction was stirred at ambient temperature for 18 h. Water (125 mL) was added to the reaction with cooling. The layers were separated and the organic phase was washed with water before evaporation. The residue was stirred with ethyl acetate (150 mL) giving a crystalline solid which was filtered off and dried under vacuum; 27.4 g, 71%. m.p.=130–131° C. M/Z=310 (M+H); 1H NMR (300 MHz, CDCl₃): 1.55 (t, 3H), 2.30 (s, 3H), 2,50 (m, 4H), 3.06 (m, 4H), 4.26 (quart. 2H), 7.08 (d, 1H), 7.90 (dd, 1H), 7.97 (d, 1H)

Preparation 3

2-Ethoxy-N-hydroxy-5-[(4-methylpiperazin-1-yl) sulfonyl]benzenecarboximidamidine

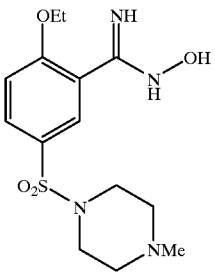

Hydroxylamine hydrochloride (20.8 g, 0.3 Mol) was added to a stirred slurry of 2-ethoxy-5-(4-methyl-1-piperazinylsulfonyl)benzonitrile (9.3 g, 0.03 Mol) in methanol (250 ml). To this mixture was added triethylamine (30.1 g, 0.3 Mol) this was washed into the reaction with methanol (50 mL) to give a solution. The reaction was allowed to stir for 90 h at room temperature before evaporation to low volume. Water (500 mL) was added and after 30 min stirring, the title compound was filtered off, washed with water and dried under vacuum to yield 8.0 g, 78%. m.p.= 183–185° C. (decomp.); M/Z=343 (M+H). 1H NMR (300 MHz, DMSO-d6): 1,38 (t, 3H), 2.14 (s, 3H), 2.50 (m, 4H), 3.30 (m, 4H), 4.20 (quart. 2H), 5.74 (s, 2H), 7.29 (dd, 1H), 7.70 (m, 2H), 9.61 (s, 1H).

Preparation 4

1-{4-Ethoxy-3-[5-(triflouromethyl)-1,2,4-oxadiazol-3-yl]phenylsulfonyl}-4-methylpiperazine

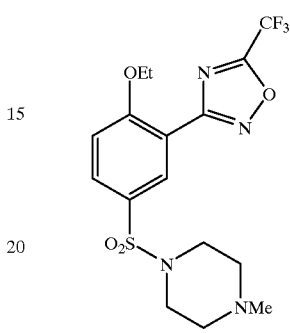

The N-hydroxyamidine prepared in preparation 3 (6.0 g, 0.0175 Mol) was added to trifluoroacetic acid (17.5 mL) at room temperature. Trifluoroacetic anhydride (17.5 mL) was then added to give a clear solution and after 2 h stirring at room temperature the reaction was evaporated at reduced pressure. Toluene was added and then the mixture was re-evaporated. On stirring the residue with methanol the product crystallised and was filtered off, washed with methanol and dried under vacuum. This yielded 7.8 g 85% of the desired product; m.p.=189–200° C. (decomp.); M/Z=421 (M+H). 1H NMR (300 MHz, DMSO-d6): 1.42 (t, 3H), 2.77 (s, 3H), 3.29 (br, m, 4H), 3.43 (br, m, 4H), 4.37 (quart. 2H), 7.58 (d, 1H), 8.08 (dd, 1H), 8.23 (d, 1H).

Preparation 5

2-ethoxy-5-(4-methyl-1-piperazinylsulfonyl) benzamidine

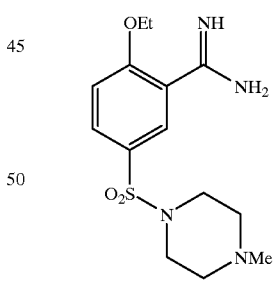

Water (4 ml) was added to a slurry of the compound prepared in preparation 4 (5.34 g, 0.01 Mol) in methanol (40 mL) at room temperature. The reaction mixture was then treated with triethylamine (2 mL) followed by Raney Ni (0.5 g). The resultant mixture was hydrogenated for 5 h at ambient temperature. After the catalyst had been filtered off, the filtrate was heated to 90° C. for 10 min and was then evaporated at reduced pressure. The residue was re-evaporated from toluene before being subjected to chromatography on silica gel eluting with toluene/methanol mixtures. Combination and evaporation of like fractions yielded 2.05 g (63%); M/Z=327 (M+H); 1H NMR (500

MHz CDCl₃/CD₃OD): 1.41 (t, 3H), 2.60 (s, 3H), 2.99 (br, m, 4H), 3.20 (br, m, 4H), 4.16 (quart. 2H), 7.10 (d, 1H), 7.77 (d, 1H), 7.82 (dd, 1H).

Preparation 6

2-ethoxy-5-(4-methyl-1-piperazinylsulfonyl) benzamidine (Preparation 5 above) can also be prepared by the following method;

Triethylaluminium (20 mL of 2M solution in hexane) was added to ammonium chloride (1.07 g, 0.2 Mol) slurried in toluene (20 mL) which had been pre-cooled to 5° C. The reaction was stirred without cooling until there was no further gas evolution when the compound prepared in preparation 2 (3.09 g, 0.1 Mol) was added. The mixture was stirred at 80° C. for 40 h. After cooling to room temperature silica gel (6 g) and dichloromethane (40 mL) were added and the mixture was stirred before filtration. The solids were washed with a methanol/dichloromethane mixture. The combined filtrate and washings were evaporated at reduced pressure to afford the product; 2.12 g 58%. Data as reported above. Preparation 7

2-ethoxy-5-(4-ethyl-1-piperazinylsulfonyl) benzonitrile

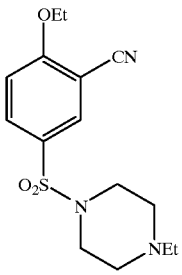

Commercially available 2-ethoxybenzonitrile (25 g, 0.17 Mol) was added dropwise to an ice cooled mixture of chlorosulfonic acid (50.8 mL, 0.765 Mol) and thionyl chloride (12.4 mL, 0.17 Mol) so as to keep the temperature below 10° C. The reaction was then stirred at ambient temperature for 18 h before being poured onto ice/water. This mixture was stirred 1 hr before the precipitated material was filtered off. The resultant solid was dissolved in acetone (300 mL) and triethylamine (25 mL, 0.179 Mol) was added followed by a slow addition of N-ethylpiperazine (25 mL, 0.198 Mol). After being left at ambient temperature for 65 h the mixture was evaporated and the residue stirred with water (1 L) for 2 h. The solids were filtered off, washed with water and dried before being chromatographed over silica gel using ethyl acetate methanol mixtures. Combination and evaporation of like fractions yielded 9.8 g, 17.8% of the title compound. Melting point=86–88° C. M/Z=324 (M+H). 300 MHz Proton NMR (CDCl3); 1.06 (t, 3H), 1.55 (t, 3H), 2.43 (q, 2H), 2.54 (m, 4H), 3.06 (m, 4H), 4.25 (q, 2H), 7.08 (d 1H), 7.90 (dd, 1H), 7.97 (d,1H).

Preparation 8

2-ethoxy-5-(4-ethyl-1-piperazinylsulfonyl) benzamidine

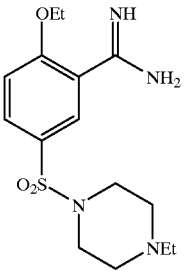

Trimethylaluminium (10 mL, 2 Molar solution in hexanes) was added dropwise to a slurry of ammonium chloride (1.07 g, 0.02 Mol) in toluene (15 mL) at 0° C. The mixture was stirred without cooling until gas evolution stopped. 2-ethoxy-5-(4-ethyl-1-piperazinylsulfonyl) benzonitrile (the compound of Preparation 7) (3.23 g, 0.01 Mol) was then added and was washed in with toluene (5 mL) before the reaction was stirred at 80° C. for 40 h. After cooling to room temperature silica gel (15 g) and dichloromethane (100 mL) were added. The mixture was then filtered and the solids were washed with dichloromethane/methanol mixtures. The combined filtrate and washings were evaporated and the residue was chromatographed over silica gel using dichloromethane methanol mixtures to afford 1.08 g, 28.6% of the title compound. M/Z=found 341 (M+H). 1H NMR (CD₃OD) 1.28 (t, 3H) 1.49 (t, 3H) 2.97 (q, 2H) 3.14 (br, s, 4H) 3.33 (br, s, 4H) 4.32 (q, 2H) 7.45 (d, 1H) 7.96 (d, 1H) 8.05 (dd, 1H).

The compounds of preparations 7 and 8 can also be used in the preparation of the compounds of published international application WO99/24433) according to a further aspect of the process of the present invention and in particular to prepare 2-[2-Ethoxy-5-(4-ethyl-piperazin-1-yl-1-sulphonyl)phenyl]-5-methyl-7-propyl-3H-imidazo[5,1-f][1,2,4]triazin-4-one also known as 1-[[3-(3,4-dihydro-5-methyl-4-oxo-7-propylimidazo[5,1-f]]-as-triazin-2-yl)-4-ethoxyphenyl]sulphonyl]-4-ethylpiperazine (the compound of examples 20, 19, 337 and 336 of WO99/24433).

What is claimed is:

1. A process for the production of a compound of general formula I:

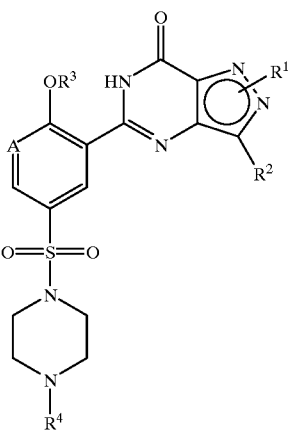

I wherein

A represents CH or N;

R¹ represents H, lower alkyl (which alkyl group is optionally interrupted by O), Het, alkylHet, aryl or alkylaryl, which latter five groups are all optionally substituted (and/or, in the case of lower alkyl, optionally terminated) by one or more substituents selected from halo, cyano, nitro, lower alkyl, $OR^5$, $C(O)R^6$, $C(O)OR^7$, $C(O)NR^8R^9$, $NR^{10a}R^{10b}$ and $SO_2NR^{11a}R^{11b}$;

$R^2$ and $R^4$ independently represent lower alkyl;

$R^3$ represents lower alkyl, which alkyl group is optionally interrupted by oxygen;

Het represents an optionally substituted four- to twelve-membered heterocyclic group, which group contains one or more heteroatoms selected from nitrogen, oxygen and sulfur;

$R^5$, $R^6$, $R^7$, $R^8$, $R^9$, $R^{11a}$ and $R^{11b}$ independently represent H or lower alkyl;

$R^{10a}$ and $R^{10b}$ either independently represent, H or lower alkyl or, together with the nitrogen atom to which they are attached, represent azetidinyl, pyrollidinyl or piperidinyl, which process comprises the reaction of a compound of formula II,

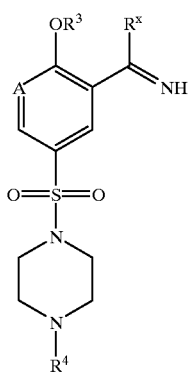

II wherein $R^x$ is a group substitutable by an aminopyrazole and A, $R^3$ and $R^4$ are as defined above, with a compound of general formula III,

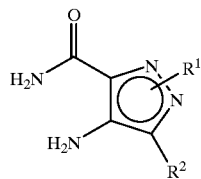

III wherein $R^1$ and $R^2$ are as defined above.

2. A process as claimed in claim 1, wherein, in the compound of general formula I, $R^1$ represents $C_{1-4}$ alkyl, which alkyl group is optionally interrupted by an oxygen atom, and/or is optionally terminated by a Het group.

3. A process as claimed in claim 2, wherein $R^1$ represents linear $C_{1-3}$ alkyl, which alkyl group is optionally interrupted by an oxygen atom, or is optionally terminated by a 2-pyridinyl group.

4. A process as claimed in claim 1, wherein, in the compound of general formula I, $R^2$ represents $C_{1-4}$ alkyl.

5. A process as claimed in claim 4, wherein $R^2$ represents linear $C_{2-3}$ alkyl.

6. A process as claimed in claim 1, wherein, in the compound of general formula I, $R^3$ represents $C_{1-5}$ alkyl, which alkyl group is optionally interrupted by an oxygen atom.

7. A process as claimed in claim 6, wherein $R^3$ represents linear or branched $C_{2-4}$ alkyl, which alkyl group is optionally interrupted by an oxygen atom.

8. A process as claimed in claim 1, wherein, in the compound of general formula I, $R^4$ represents $C_{1-3}$ alkyl.

9. A process as claimed in claim 8, wherein $R^4$ represents $C_{1-2}$ alkyl.

10. A process as claimed in claim 1, wherein the compound is selected from sildenafil, or any one of the following four compounds

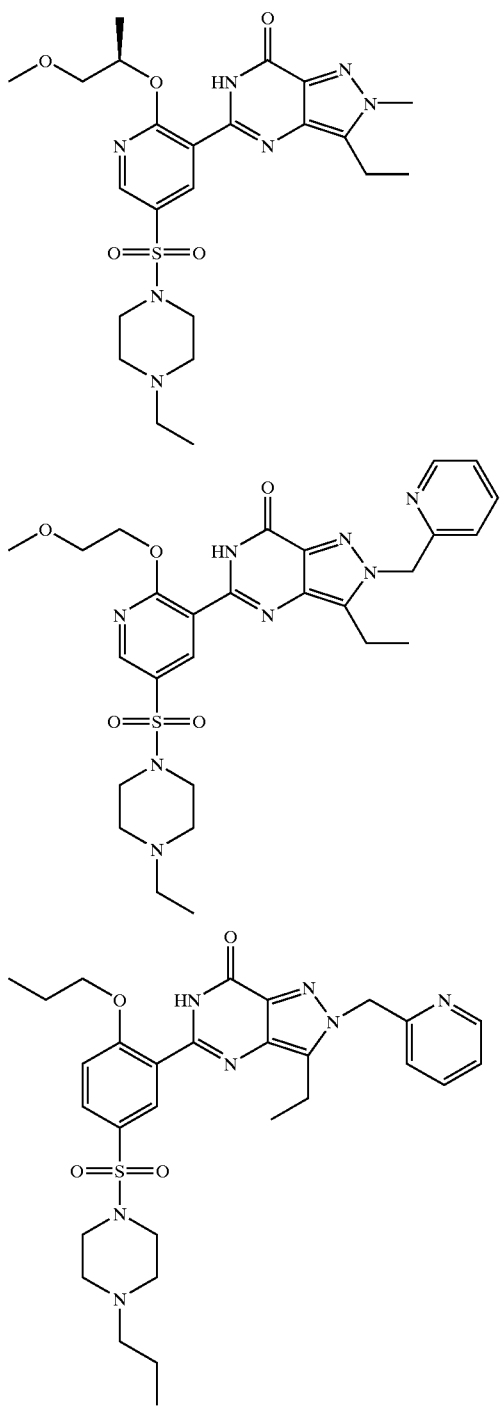

-continued

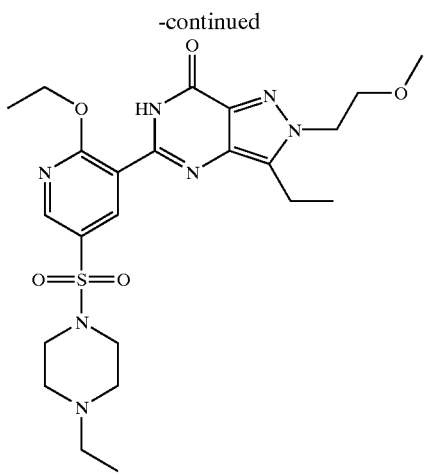

11. A process as claimed in claim 1, wherein the group $R^x$ of the compound of formula II represents —$NH_2$, —$NHR^a$, —$N(R^b)R^c$, —$SR^d$, —SH, —$OR^e$ (in which groups $R^a$ to $R^e$ each independently represent the same groups that $R^1$ as defined in claim 1 may represent, except that they do not represent H) or halo.

12. A process as claimed in claim 11, wherein $R^x$ represents —$NHR^a$, —$N(R^b)R^c$, —$SR^d$, —SH or —$OR^e$.

13. A process as claimed in claim 12, wherein $R^x$ represents ethoxy.

14. A process as claimed in claim 1, wherein the reaction is carried out in the presence of a solvent system that includes an aromatic hydrocarbon, chlorobenzene or a solvent of formula $R^xH$, wherein $R^x$ is as defined in claim 1.

15. A process as claimed in claim 14, wherein the solvent is toluene, xylene, chlorobenzene or ethanol.

16. A process as claimed in claim 14, wherein the reaction is carried out at reflux temperature.

\* \* \* \* \*